(12) United States Patent
Rousseau

(10) Patent No.: US 7,959,878 B2
(45) Date of Patent: Jun. 14, 2011

(54) UNIT CUVETTE FOR ANALYZING A BIOLOGICAL FLUID, AUTOMATIC DEVICE FOR IN VITRO ANALYSIS

(75) Inventor: Alain Rousseau, Paris (FR)

(73) Assignees: Immunodiagnostic System France, Pouilly en Auxois (FR); Alain Rousseau, Paris (FR)

( * ) Notice: Subject to any disclaimer, the term of this patent is extended or adjusted under 35 U.S.C. 154(b) by 129 days.

(21) Appl. No.: 12/087,492

(22) PCT Filed: Jan. 17, 2007

(86) PCT No.: PCT/FR2007/000084
§ 371 (c)(1),
(2), (4) Date: Sep. 16, 2008

(87) PCT Pub. No.: WO2007/085715
PCT Pub. Date: Aug. 2, 2007

(65) Prior Publication Data
US 2009/0117005 A1 May 7, 2009

(30) Foreign Application Priority Data
Jan. 25, 2006 (FR) ...................................... 06 00670

(51) Int. Cl.
*B01L 3/00* (2006.01)
(52) U.S. Cl. .............................. 422/554; 422/63; 422/64
(58) Field of Classification Search ................. 422/63, 422/64, 547, 548, 549, 554
See application file for complete search history.

(56) References Cited

U.S. PATENT DOCUMENTS

| | | | |
|---|---|---|---|
| 3,538,962 A * | 11/1970 | Gilson | 141/131 |
| 4,785,407 A | 11/1988 | Sakagami | |
| 4,918,984 A * | 4/1990 | Martinoli et al. | 73/64.43 |
| 5,350,564 A | 9/1994 | Mazza et al. | |
| 5,885,529 A * | 3/1999 | Babson et al. | 422/65 |
| 6,106,781 A | 8/2000 | Rosenberg | |
| 6,767,511 B1 | 7/2004 | Rousseau | |
| 2004/0048361 A1 | 3/2004 | Isobe et al. | |

FOREIGN PATENT DOCUMENTS

| | | |
|---|---|---|
| EP | 0 325 874 A1 | 8/1989 |
| EP | 1 382 392 A1 | 1/2004 |
| JP | U-58-80564 | 5/1983 |
| JP | A-59-147267 | 8/1984 |
| JP | A-2-45763 | 2/1990 |
| JP | A-8-43400 | 2/1996 |

(Continued)

*Primary Examiner* — Jill Warden
*Assistant Examiner* — Dwayne K Handy
(74) *Attorney, Agent, or Firm* — Oliff & Berridge, PLC

(57) ABSTRACT

The bottom of the cuvette comprises a curved raceway placed so as to guide the oscillating movement of a ball inserted into the cuvette. In addition, the cuvette comprises means of attachment, in two perpendicular directions, to adjacent unit cuvettes. The cuvettes can thus be stored as plates in a feed magazine of an analytical device. The analytical device comprises several stations placed around a rotary ring. Only where it is desired to determine the clotting time of the blood contained in the cuvette a ball is introduced into the latter, at a ball distribution post. The cuvette equipped in this way is then brought to a station where the test is carried out. The major advantage of the invention is the polyvalence of the cuvette and of the analytical device.

9 Claims, 4 Drawing Sheets

FOREIGN PATENT DOCUMENTS

| | | |
|---|---|---|
| JP | A-11-223633 | 8/1999 |
| WO | WO 88/02866 A1 | 4/1988 |
| WO | WO 92/04978 A1 | 4/1992 |
| WO | WO 92/14550 A1 | 9/1992 |
| WO | WO 93/02364 A1 | 2/1993 |
| WO | WO 99/64839 A1 | 12/1999 |

* cited by examiner

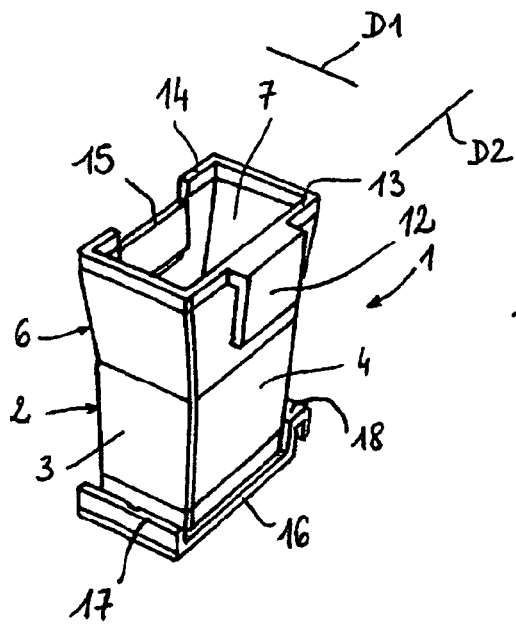
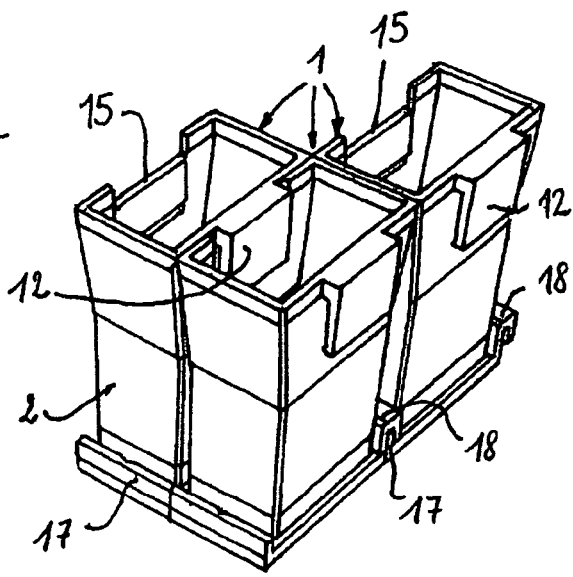
FIG. 1　　　　　　　　FIG. 4
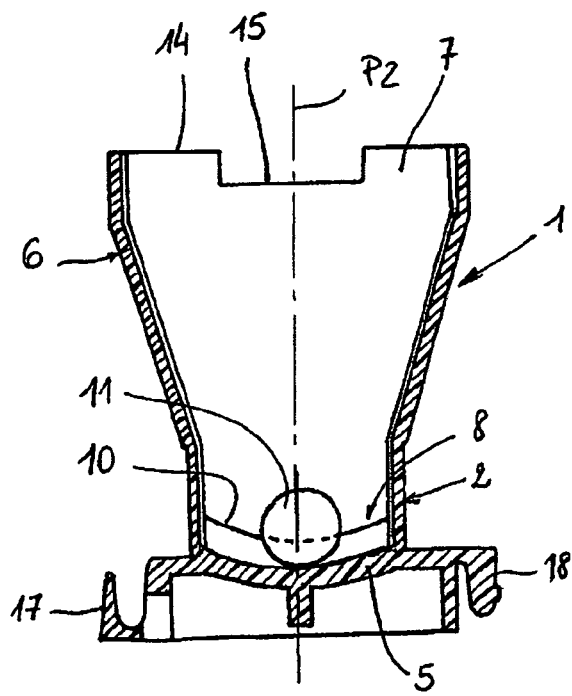
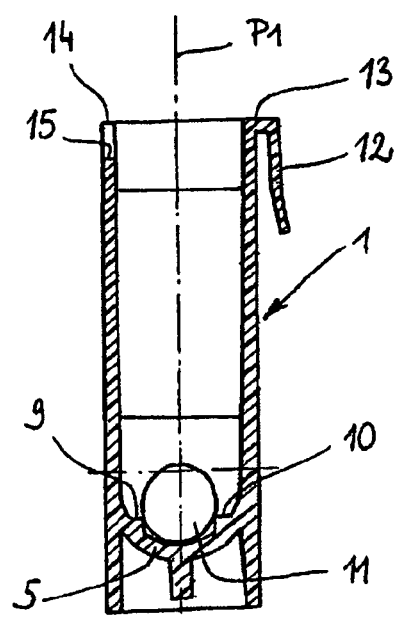
FIG. 2　　　　　　　　FIG. 3

UNIT CUVETTE FOR ANALYZING A BIOLOGICAL FLUID, AUTOMATIC DEVICE FOR IN VITRO ANALYSIS

BACKGROUND OF THE INVENTION AND DESCRIPTION OF THE PRIOR ART

The present invention relates to a unit cuvette capable of containing a biological fluid, in order to analyze said fluid, and to an automatic analyzer comprising such cuvettes for in vitro analysis.

Document EP 0 325 874 teaches a cuvette for determining the clotting time of blood. For this purpose, the bottom of the cuvette comprises a curved raceway with an upwardly directed concavity, on which a ferromagnetic ball is placed and driven in a periodic movement under the effect of an external magnetic field. By detecting the variations in amplitude and/or frequency of the movement of the ball it is possible to measure the clotting time. This measurement is carried out by means of a densitometer placed in such a way that the light beam that it produces is approximately tangential to the ball when it is at the lowermost point of the raceway. The cuvettes may be used either individually or in blocks of several cuvettes.

This type of cuvette, although generally satisfactory, nevertheless has a number of drawbacks.

Firstly, when the cuvettes disclosed in document EP 0 325 874 are used individually, it is difficult or time-consuming to store them in an ordered manner, which saves space, without it being tricky to separate the cuvettes from one another by means of a controller. Conversely, when several cuvettes are formed as a single block, storage is easier, even if a greater volume may be required. However, handling such a block may prove awkward in certain applications and, in any case, it is difficult if not impossible to carry out different tests on the cuvettes of a given block, unless a very specific analyzer is provided.

Furthermore, these cuvettes are solely intended for determining the clotting time of blood and, for this purpose, they all have a ball. Of course, it is possible to use these cuvettes for performing other analyses or measurements on the biological fluid that they contain, but this involves the following drawbacks:

- the cost of a cuvette is needlessly increased because of the unnecessary presence of a ball on the one hand, and means provided on the cuvette for preventing the ball from escaping on the other;
- the presence of a ball may prove problematic in the case of certain tests (especially immunology tests using magnetic particles); and
- in the case of photometric measurements, it is necessary to increase the reaction volume so as to cover the ball with a sufficient height so as to carry out the optical measurement escaping the ball. The cost of the test is therefore increased owing to unnecessary amounts of reactants.

The present invention aims to remedy the abovementioned drawbacks.

SUMMARY OF THE INVENTION

For this purpose, and according to a first aspect, the invention relates to a unit cuvette capable of containing a biological fluid for analyzing said fluid, comprising, substantially on its bottom, means defining a curved raceway, the concavity of which is upwardly directed, said raceway having its lowest point approximately at its center and being designed to guide the oscillating movement of a ball inserted into the cuvette, wherein it includes attachment means for attaching, in a first direction to at least one other unit cuvette and attachment means for attaching, in a second direction, approximately perpendicular to the first, to at least one other unit cuvette.

Several cuvettes according to the invention can therefore be assembled together so as to form trays that are very easy to store, in a confined space. In addition, it is very easy to detach a unit cuvette from such a tray, even automatedly, thereby making this type of cuvette particularly easy to use in an automatic analyzer for in vitro analysis.

Moreover, these cuvettes are multipurpose cuvettes. This is because they include a raceway for measuring the clotting time of blood by detecting the movements of a ball. However, the presence of a ball is optional, and the cuvette can be used for any type of test, without the impediment due to the ball or to the particular shape of the bottom of the cuvette. The presence of a lowermost point in the bottom of the cuvette, formed by the raceway, has in addition the advantage of allowing liquids to be drawn in with a very small dead volume and of making it easier to wash the magnetic particles.

The invention therefore provides a cuvette that is particularly useful when it is used in an automatic analyzer for in vitro analysis since cuvettes of one and the same type, stored in tray form in a single magazine, mean that various tests can be carried out depending on the requirements (biochemistry, immunochemistry, coagulation).

According to one possible embodiment, the attachment means of the cuvette along the first direction comprise at least a downwardly directed tab provided on one of the edges of the upper part of the cuvette. Furthermore, a notch may be provided on the edge of the upper part of the cuvette on the opposite side from the edge having the tab, the tab of a cuvette being intended to cooperate with the notch of an adjacent cuvette along the first direction.

The attachment means of the cuvette along the second direction comprise for example two overhangs, one of which forms an upwardly open hook and the other forms a downwardly open hook, the upwardly open hook of one of the overhangs of a cuvette being capable of engaging with the downwardly open hook of the overhang of an adjacent cuvette, the overhangs being provided on the base of the cuvette along two opposed edges orthogonal to the upper edge of the cuvette having the tab.

According to a second aspect, the invention relates to an automatic analyzer for in vitro analysis, comprising:

- a feed magazine in which an array of unit cuvettes as described previously is stored;
- a rotor of approximately vertical axis, associated with rotational drive means and having a horizontal toothed ring defining cavities that are open radially to the outside and capable of receiving the unit cuvettes, in particular from the feed magazine;
- a device for introducing biological fluid to be analyzed into at least one cuvette;
- stations placed around the ring, for carrying out measurements and/or analyses on the fluid contained in a cuvette, at least one of said stations having means for loading/unloading the cuvettes for carrying out a measurement and/or an analysis at the station, away from the ring; and
- a controller, controlled by incorporated software for managing the sequences of the desired process for each cuvette.

Thanks to this automatic analyzer and the cuvettes used, which can serve for various types of test using different measurement technologies, it is possible to carry out these various tests and to control them in an improved manner compared with the prior art. This is because processes involving lengthy (immunology) measurements or those requiring the continuous observation of the phenomenon (clotting) to be measured may be carried out away from the ring, on the corresponding stations, and therefore do not constitute bottlenecks in the case of rapid-process (biochemistry) tests. The cuvettes may be stored in tray form in the feed magazine, while still being easily detachable from one another, on demand.

The automatic analyzer according to the invention is multipurpose, but simple and inexpensive to manufacture and to maintain. Furthermore, its operating cost is substantially lower than that of the controllers of the prior art. This means that the number of machines per laboratory can be reduced, thus helping to reduce the public health expenditure.

Advantageously, the device includes a station for delivering ferromagnetic balls, which is placed close to the ring so as to be able to insert a ball into a cuvette placed in a cavity, and a station for determining the time required for the physical state of the biological fluid contained in said cuvette to be modified by making the ball undergo an oscillating movement on the raceway provided in the cuvette.

Thus, it is possible to bring one of the cuvettes, taken from the array of identical and multipurpose unit cuvettes stored in the feed magazine, via the toothed ring, opposite the ball delivery station, where it receives a ball. The cuvette thus provided is then directed towards the station for determining the time required for the physical state of the biological fluid contained in said cuvette to be modified, for example the station for determining the clotting time of blood. Therefore, a ball is introduced into the cuvette according to the requirements of the tests to be carried out, and not systematically, this being advantageous especially in terms of cost.

BRIEF DESCRIPTION OF THE DRAWINGS

One possible embodiment of the invention will now be described, by way of non-limiting example, with reference to the appended figures, in which:

FIG. 1 is a perspective view of a cuvette according to the invention;

FIG. 2 is a longitudinal sectional view of the cuvette;

FIG. 3 is a cross-sectional view of the cuvette;

FIG. 4 is a perspective view of three cuvettes joined together;

DESCRIPTION OF THE PREFERRED EMBODIMENT

Figure 5:
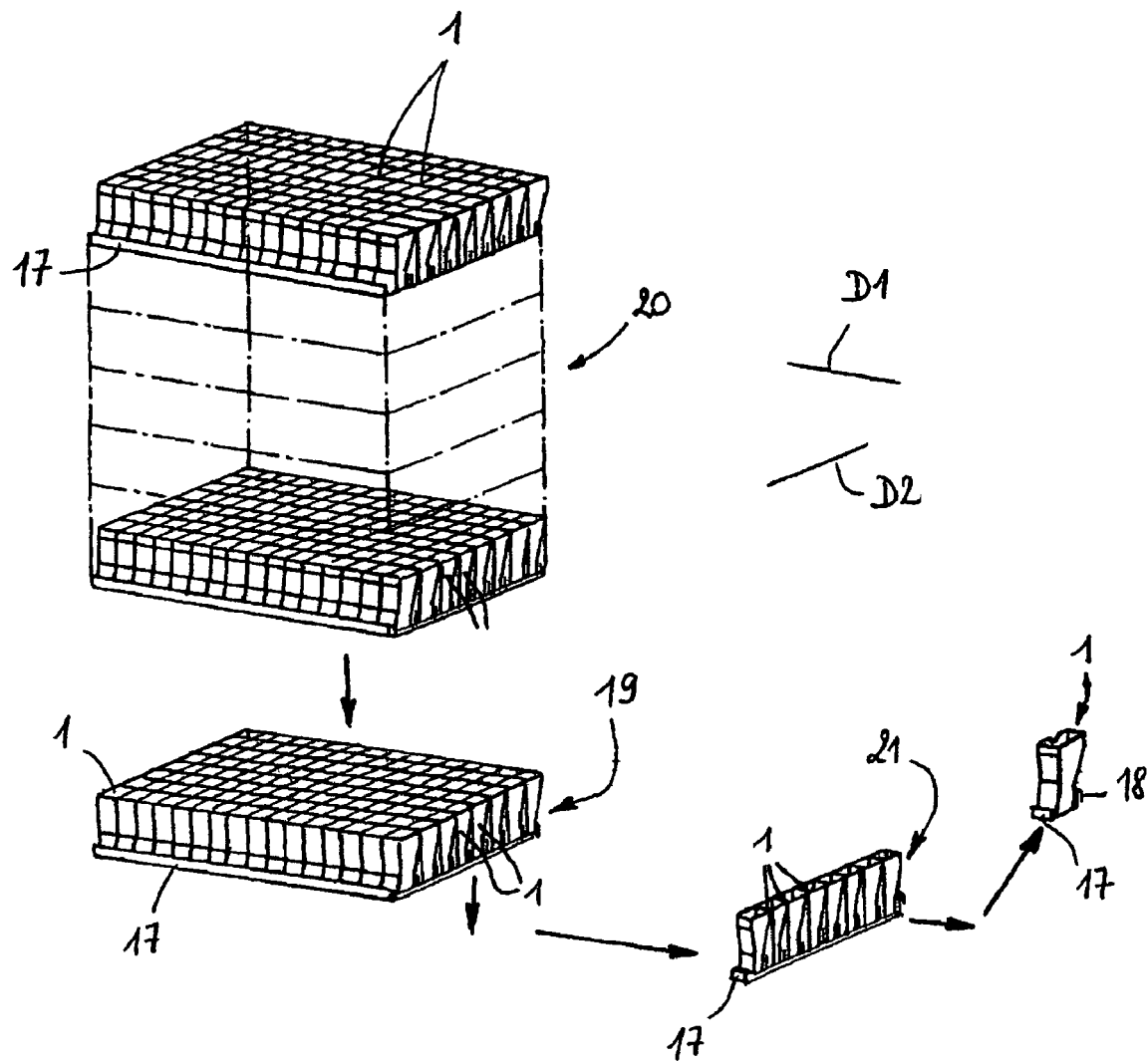
FIG. 5 is a perspective view of a stack of trays of cuvettes and the kinematic system for detaching the cuvettes from one another.

As illustrated in FIG. 1, a cuvette 1 has a lower part 2 of approximately parallelepipedal shape, having large faces 3, small faces 4 and a bottom 5. The lower part 2 has a length of around 8 mm and a width of around 4 mm. This makes it possible to obtain a reaction mixture with a minimum volume of 200 µl, thereby limiting the consumption of reactants, while still maintaining optical paths sufficient for the spectrophotometric and turbidimetric (clotting) measurements.

The lower part 2 of the cuvette 1 is extended by a funnel-shaped upper part 6 flaring out on the opposite side from the bottom 5, in the form of a truncated cone or truncated pyramid, and forming an upper opening 7. This makes it possible to increase the rinsing volume or the reaction volume, to create a wide opening and to make it easier to rinse the nanoparticles for immunology tests. A cuvette 1 having a height of around 22 mm may contain up to 650 µl.

The transverse direction D1 is defined as the direction orthogonal to the large faces 3 and the longitudinal direction D2 as the direction orthogonal to the small faces 4. The longitudinal mid-plane and the transverse mid-plane of the cuvette 1 are also defined as P1 and P2 respectively (see FIGS. 2 and 3).

The cuvette will be described in a position in which the bottom 5 is approximately horizontal and located below the opening 7.

The bottom 5 of the cuvette 1 has a low point located at the intersection of the planes P1 and P2, thereby enabling almost the entire liquid contained in the cuvette 1 to be removed by suction, leaving a very small volume remaining in the cuvette. In the exemplary embodiment, the bottom 5 of the cuvette 1 is a portion of a cylinder whose axis is approximately parallel to D1.

A curved raceway 8, the concavity of which is upwardly directed, is provided substantially in the bottom of the cuvette 1. The raceway 8 has the form of a portion of a cylinder, with a radius between 8 and 10 mm, the axis of said cylinder here being approximately parallel to D1 and contained in the plane P2. The raceway 8 is therefore elongate in the longitudinal direction of the lower part 2 of the cuvette 1 and has its lowermost point approximately at its center. The raceway 8 is defined by two lateral rails 9, 10 provided in the lower part of the cuvette 1, close to the bottom 5. These two rails 9, 10 make it possible to guide the oscillating movement of a ball 11 inserted into the cuvette 1. The dimensions of the ball 11 are adapted so that it rests on the rails 9, 10, but not on the bottom 5 so as to limit friction. The ball 11 has for example a diameter between 1 and 2.5 mm.

The cuvette 1 and the rails 9, 10 are made as one piece by molding a transparent plastic compatible with the various reactions for analyzing the biological fluid that the cuvette is able to contain. A suitable material is polypropylene, but any other plastic having transparency properties sufficient for the optical density measurement and not having too great an affinity with proteins may be suitable.

In its upper part 6, the cuvette 1 has a downwardly directed flexible tab 12 projecting from one of its longitudinal upper edges 13. On the opposed upper longitudinal edge 14, the cuvette 1 has a notch 15 with dimensions adapted to those of the tab 12. The tab 12 of a cuvette 1 is intended to cap the notch 15 of an adjacent cuvette 1 (in the direction D1) so as to attach two cuvettes 1 as shown in FIG. 4.

Furthermore, the cuvette 1 has a base 16 in the lower part, in which there are provided, along two opposed edges parallel to the direction D1, a first overhang 17 forming an upwardly open hook and a second overhang 18 forming a downwardly open hook. The upwardly open hook of the first overhang 17 is designed to engage with the downwardly open hook of the second overhang 18 of an adjacent cuvette 1 (along the direction D2), in order to attach two cuvettes 1 as shown in FIG. 4.

Thanks to the attachment means in the two directions D1 and D2, it is possible to attach cuvettes 1 to one another, manually or automatically, so as to form trays 19, as illustrated in FIG. 5. Furthermore, the overhangs 17, 18 make it possible to have overall dimensions of the cuvettes 1 which are the same in their upper parts 6 and in their lower parts 2 in such a way that, when assembled together, the cuvettes 1 constitute a flat tray. This makes it possible to order the cuvettes 1 so as to store them in a simple and compact manner, whilst still allowing a cuvette 1 to be easily detached from the tray 19.

FIG. 5 shows superposed trays 19 of cuvettes 1 in the form of a stack 20. The lower tray may be released by simply displacing it vertically relative to the other trays of the stack. It is then possible to disengage a row 21 by vertical displacement of the cuvettes in this row 21 relative to the other cuvettes in the same tray. Finally, a cuvette 1 may be separated from the other cuvettes in the same row 21 by a transverse displacement.

An automatic analyzer 22 for in vitro analysis illustrated in FIGS. 6 to 8 will now be described.

Figure 6:
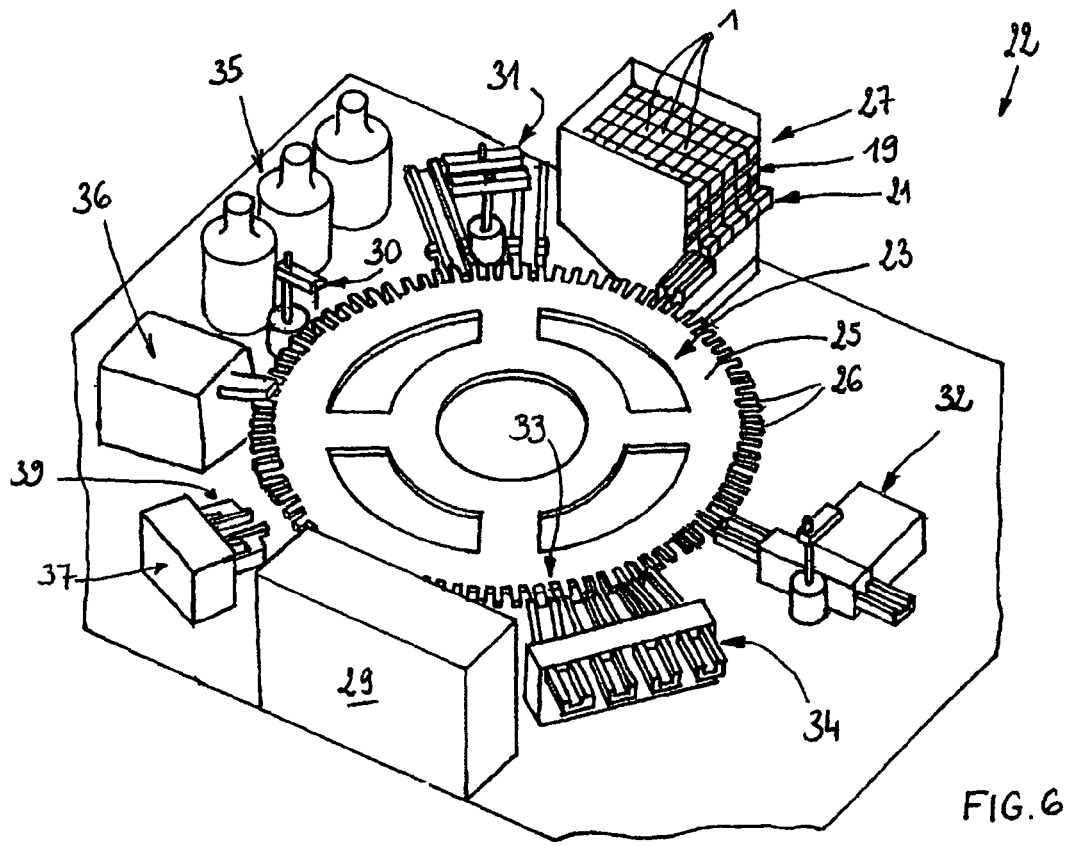
FIG. 6 is a schematic perspective view of the automatic analyzer for in vitro analysis, showing the toothed ring and the various stations placed around this ring.
Figure 7:
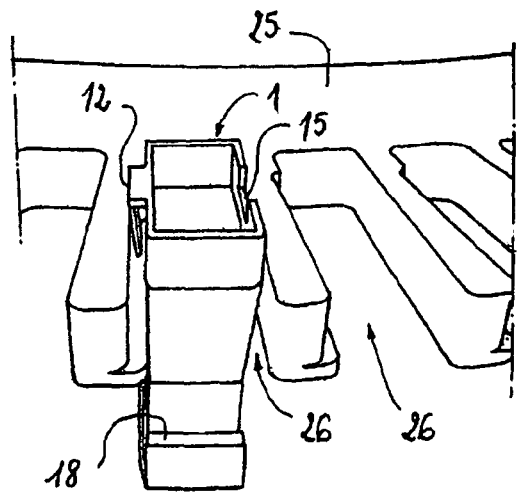
FIG. 7 is a perspective view of a cuvette engaged in a cavity of the ring.

The analyzer 22 comprises a storage/sampling first part (not shown), for storing and taking specimens of a biological fluid, and a measurement/analysis second part illustrated in FIG. 6. A device for sampling and pipetting the specimens and the reactants is used to deposit these in cuvettes 1 placed in the second part of the analyzer 22, for the purpose of conducting various tests.

The analyzer 22 includes a rotor 23 mounted so as to pivot about its vertical axis 24 and driven by a motor (not shown). Fastened to the rotor 23 is a toothed ring 25 defining cavities 26 opening radially to the outside, into which the cuvettes 1 are intended to be inserted. For this purpose, and as illustrated in FIG. 7, the width of a cavity 26 of the toothed ring 25 is approximately equal to the width of the cuvette 1 in its upper part with the tab 12. Consequently, when the cuvette 1 is engaged in a cavity 26, the tab 12 is applied against the wall of the cavity 26 and immobilizes the cuvette 1 by a spring effect in such a way that said cuvette cannot move while the rotor 23 is rotating, thus making it possible to make stable optical measurements. The tab therefore has two functions, namely to attach two adjacent cuvettes 1 and keep a cuvette 1 in place in a cavity 26.

Arranged around the ring 25 are radially oriented stations for carrying out various measurements, tests or analyses on the biological fluid contained in the cuvettes 1, and also a feed magazine 27.

Figure 8:
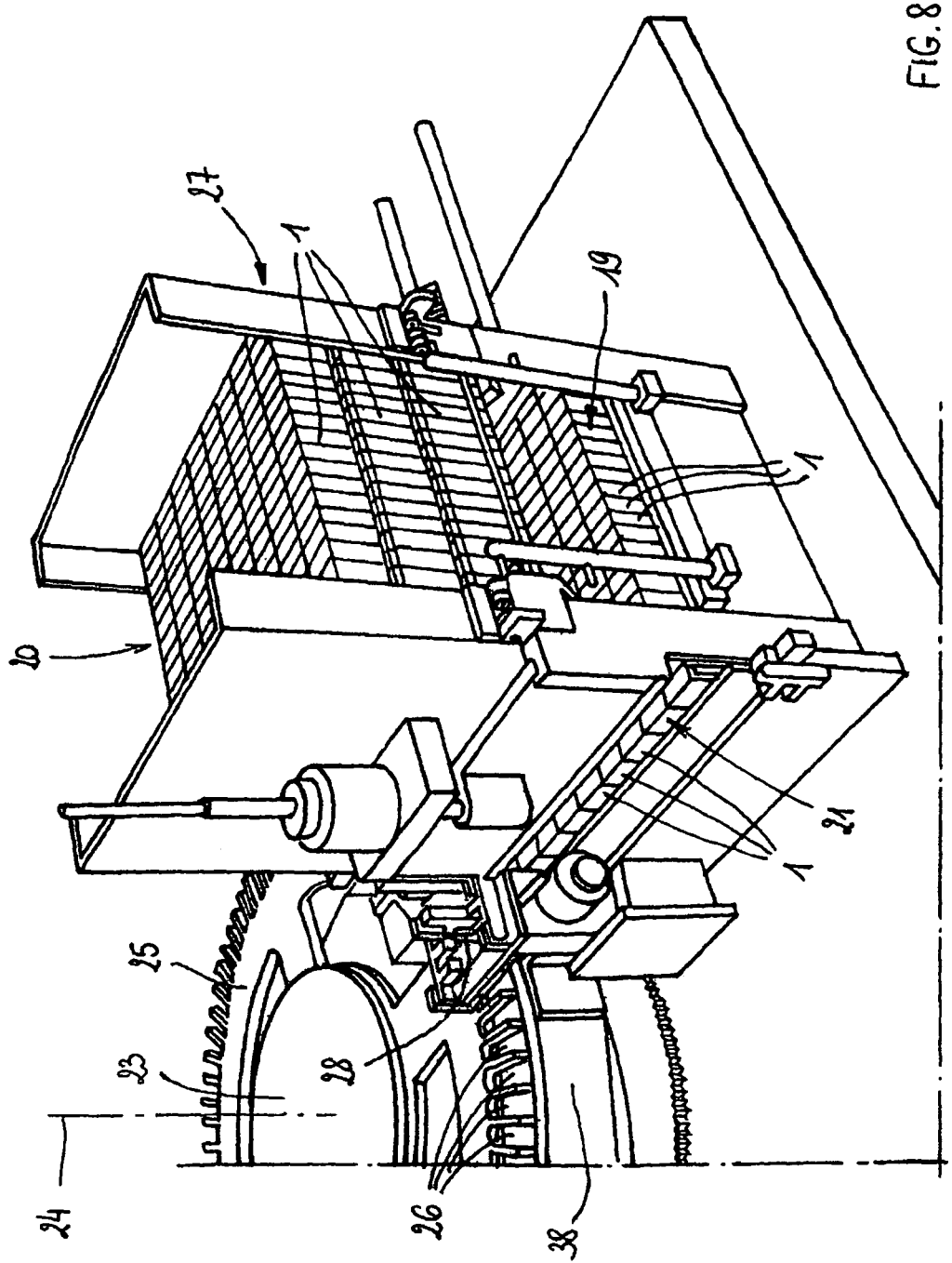
FIG. 8 is a perspective view of the cuvette feed magazine.

As illustrated in FIG. 8, the feed magazine 27 comprises a stack 20 of trays 19 of unit cuvettes 1 assembled together thanks to the attachment means. A cuvette 1 may be released according to the kinematic system described with reference to FIG. 5: the lower plate 19 drops onto a support, is then pushed to the left (in FIG. 8) until a row 21 can be shifted downward and detached from the rest of the tray 19. Next, the row 21 is pushed toward the ring 25, after which the first cuvette 1 is disengaged transversely from the others by a pusher, which brings it into line with a second pusher 28 transverse to the first pusher, enabling the cuvette 1 to be pushed into a cavity 6 of the ring 25.

As a nonlimiting example, the stations arranged around the ring 25 may be:
- a station 29 for the photometric measurement;
- a station 30 for delivering avidin-grafted or streptavidin-grafted magnetic nanoparticles for immunocapture reactions;
- a station 31 for magnetic sedimentation and for washing;
- a station 32 for luminescence development and reading;
- a station 33 comprising four aliquoting or diluting substations;
- a station 34 for removing spent cuvettes to a waste container, the station 34 here being placed in such a way that the cuvettes to be removed pass via the station 33 after being extracted from the ring 25;
- a station 35 for ancillary reactants or for magnetic particles; for the development of the luminance; or for the decontamination and desorption of proteins in the tubings of the sampling system;
- a station 36 for delivering ferromagnetic balls 11;
- a station 37 for determining the time required for the physical state of the biological fluid contained in the cuvette 1 to be modified, employing an oscillating movement of the ball 11 on the raceway 8 provided in the cuvette 1; and
- a well for rinsing and/or decontaminating sampling and delivering needles (not shown).

The ring 25 moves above a torroidal element 38 having an upwardly open U-shaped cross section (see FIG. 8). The temperature-regulated volume, for example one regulated to 37° C., is thus defined between the ring 25 and the torroidal element 38, in which volume the cuvettes 1 can move under the action of the ring 25. The torroidal element 38 has a number of openings provided at least in its outer wall and arranged facing the stations requiring the introduction and/or extraction of the cuvettes 1. A linear actuator, such as an actuating cylinder, mounted on the torroidal element 38 or on the support for the station in question, enable a cuvette 1 to be moved between the ring 25 and the station in question.

The operation of the analyzer 22 is as follows.

An operator indicates, on a computer control system connected to the analyzer 22, the measurements and tests to be carried out on a biological fluid specimen taken. Embedded software is used to manage the movements of an automatic controller for the purpose of carrying out several analyses sequentially but in parallel. The operator has beforehand loaded the reactants, identifying them for example using a barcode reader.

The feed magazine 27 introduces the required number of empty cuvettes 1 into cavities 26 of the ring 25. The cuvettes 1, into which the biological fluid and the possible appropriate reactants have been introduced, are brought, by rotation of the ring 25, opposite the stations corresponding to the tests or measurements to be carried out. Depending on the circumstances, the cuvette 1 is discharged to the station in order for the analysis to take place (and may remain there for the necessary time without stopping the movement of the ring 25, which simultaneously transfers or holds in position other cuvettes to other measurement/analysis stations), or the analysis is carried out while the cuvette 1 is still placed in a cavity 26. Thus, the analyses requiring a relatively long time may be carried out in parallel, at a precise station, whereas other, instantaneous, analyses are carried out at other stations. Once the analysis has been completed, the cuvettes 1 are, where necessary, replaced on the ring 25, which brings them to the removal station 34.

The ring 25 is therefore a device for not only moving the cuvettes 1 but also carrying out generally rapid biochemical tests. The ring 25 has a sufficient number of cavities 26 to be able to manage, simultaneously, all the cuvette transfers and reaction incubations for all disciplines so as to obtain the desired specimen processing rates.

As regards the determination of the time required for the physical state of the biological fluid contained in the cuvette 1 to be modified, in particular the clotting time of blood, the procedure is as follows.

When such a determination has to be performed, and only in this case, the ring 25 firstly brings a cuvette 1 to the station 36 for delivering ferromagnetic balls 11. A ball 11 is then introduced into the cuvette 1, which is then moved to the station 37 where the measurement is carried out.

The station 37 includes means 39 for exciting the ball 11 with magnetic pulses and for detecting the amplitudes of oscillation of the ball 11. Thus, the ball 11 is made to undergo, in a known manner, a periodic movement along the raceway 8 under the effect of an external magnetic field, at a frequency close to the natural frequency of the ball (around 2.5 to 5 Hz). The system behaves as a microviscometer. When the viscosity of the medium is not changing, the amplitude of the ball 11 is constant. When the viscosity increases, owing to the fact that the excitation frequency is close to the natural frequency, the amplitude very rapidly decreases and allows precise detection, by measuring the amplitude of the ball, the onset of clotting reactions or the presence of very loose clots. In particular, this system makes it possible to measure very small fibrinogen levels very accurately.

Thus, the invention makes a key improvement to the prior art by providing a unit cuvette and an analyzer which are multipurpose, are of simple design and implementation and enable operating costs to be reduced.

It goes without saying that the invention is not limited to the exemplary embodiment described above, but on the contrary it embraces all alternative embodiments thereof. In particular, it should be noted that the tab and the notch could be placed on transverse edges of the cuvette and the overhangs on longitudinal edges of the cuvette.

The invention claimed is:

1. A unit cuvette capable of containing a biological fluid for analyzing the biological fluid, the cuvette comprising:
   means defining a curved raceway located substantially on a bottom of the cuvette,
      the curved raceway having a concavity that is upwardly directed,
      the curved raceway having a lowest point located approximately at a center of the curved raceway, and
      the curved raceway designed to guide an oscillating movement of a ball inserted into the cuvette;
   attachment means for attaching the cuvette to a first other unit cuvette in a first direction comprising at least a downwardly directed tab provided on an edge of an upper part of the cuvette; and
   attachment means for attaching the cuvette to a second other unit cuvette in a second direction that is approximately perpendicular to the first direction, comprising:
      a first overhang that forms an upwardly open hook, and
      a second overhang that forms a downwardly open hook, wherein:
      the upwardly open hook is capable of engaging with the downwardly open hook of an adjacent cuvette, the overhangs being provided on a base of the cuvette along two opposed edges orthogonal to the upper edge of the cuvette having the tab.

2. The cuvette as claimed in claim 1, wherein the cuvette has a notch provided on an edge of the upper part of the cuvette opposite from the edge having the tab.

3. The cuvette as claimed in claim 1, wherein the cuvette and the means defining the curved raceway are a single piece of a transparent plastic compatible with various reactions for analyzing the biological fluid.

4. The cuvette as claimed in claim 1, further comprising a lower part having an approximately parallelepipedal shape elongate in a direction of the curved raceway, the lower part being extended by a funnel-shaped upper part flaring out on a side opposite from the bottom.

5. The cuvette as claimed in claim 1, wherein the curved raceway takes a form of a portion of a cylinder having a radius between 8 and 10 mm, for a ball having a diameter between 1 and 2.5 mm.

6. The cuvette as claimed in claim 1, wherein the means defining the curved raceway comprise two lateral rails provided in a lower part of the cuvette.

7. An automatic analyzer for in vitro analysis, the analyzer comprising:
   at least one unit cuvette of claim 1;
   a feed magazine configured to store an array of unit cuvettes;
   a rotor of approximately vertical axis, associated with rotational drive means and having a horizontal toothed ring defining cavities that are open radially to an outside and capable of receiving the unit cuvettes from a feed magazine;
   a device for introducing biological fluid to be analyzed into at least one cuvette;
   stations placed around the ring, configured for carrying out measurements and/or analyses on the biological fluid contained in the cuvette, at least one of the stations having means for loading/unloading the cuvettes for carrying out a measurement and/or an analysis at the station, away from the toothed ring; and
   a controller, controlled by incorporated software for managing sequences of a desired process for each cuvette.

8. The analyzer as claimed in claim 7, wherein the attachment means of the cuvette along the first direction comprise at least a downwardly directed tab provided on an edge of an upper part of the cuvette and a width of the cavity of the toothed ring is approximately equal to the width of the upper part of the cuvette with the tab.

9. The analyzer as claimed in claim 7, further comprising a station for delivering ferromagnetic balls, the station being placed close to the toothed ring so as to be able to insert the ferromagnetic ball into the cuvette placed in the cavity, and a station for determining a time required for a physical state of the biological fluid contained in the cuvette to be modified by making the ferromagnetic ball undergo the oscillating movement on the curved raceway provided in the cuvette.

* * * * *